(12) United States Patent
Sherry et al.

(10) Patent No.: US 8,147,497 B2
(45) Date of Patent: Apr. 3, 2012

(54) IN SITU PATELLAR FIXING SYSTEM

(75) Inventors: Eugene Sherry, Alexandria (AU); Sureshan Sivananthan, Wimbledon (GB); Patrick Hans Heinrich Warnke, Augustfehn (DE); Patrick White, West Chester, PA (US); Fabrice Chenaux, Exton, PA (US)

(73) Assignee: Greatbatch Medical S.A., Orvin (CH)

( * ) Notice: Subject to any disclaimer, the term of this patent is extended or adjusted under 35 U.S.C. 154(b) by 1008 days.

(21) Appl. No.: 12/040,778

(22) Filed: Feb. 29, 2008

(65) Prior Publication Data

US 2008/0228190 A1    Sep. 18, 2008

Related U.S. Application Data

(60) Provisional application No. 60/892,629, filed on Mar. 2, 2007.

(51) Int. Cl.
 *A61B 17/58* (2006.01)
 *A61F 5/00* (2006.01)
(52) U.S. Cl. .......................................... 606/88
(58) Field of Classification Search ............... 606/86 R, 606/87–89, 79–85, 96–99; 623/20.14–20.36
See application file for complete search history.

(56) References Cited

U.S. PATENT DOCUMENTS

| | | | | |
|---|---|---|---|---|
| 5,021,055 A * | 6/1991 | Burkinshaw et al. | ........... | 606/82 |
| 5,129,908 A * | 7/1992 | Petersen | ........................ | 606/88 |
| 5,147,365 A * | 9/1992 | Whitlock et al. | ............... | 606/88 |
| 5,284,482 A * | 2/1994 | Mikhail | ...................... | 606/86 R |
| 5,542,947 A * | 8/1996 | Treacy | ............................. | 606/88 |
| 5,643,272 A * | 7/1997 | Haines et al. | ................... | 606/80 |
| 6,645,215 B1 * | 11/2003 | McGovern et al. | ........... | 606/102 |
| 7,488,324 B1 * | 2/2009 | Metzger et al. | ................. | 606/89 |
| 7,935,151 B2 * | 5/2011 | Haines | ....................... | 623/20.35 |
| 2005/0149038 A1 * | 7/2005 | Haines et al. | ................... | 606/87 |
| 2007/0233142 A1 * | 10/2007 | Oliver | ............................ | 606/88 |

* cited by examiner

*Primary Examiner* — Thomas C. Barrett
*Assistant Examiner* — Christopher Beccia
(74) *Attorney, Agent, or Firm* — Michael F. Scalise (57) ABSTRACT

Disclosed is a patellar cutting jig for use in a knee joint surgical procedure. The jig grips and holds a patella in situ in spatial reference to the femur to enable the appropriate cut to be made to the patella to accurately accommodate the patello-femoral gap at the replacement knee joint. The patella jig has a referencing component that provides a landmark connection between the patella jig and the femur which enables the patella clamp of the jig to be oriented relative to the reference feature prior to gripping the patella. Thus a patella held in the clamp is fixed in the cutting jig an appropriate orientation relative to the femur prior to its resection. Cutting the patella while it is referenced to the patellar groove on the femur increases the accuracy of the resection.

19 Claims, 13 Drawing Sheets

IN SITU PATELLAR FIXING SYSTEM

The present application claims the benefit of prior filed U.S. Provisional application Ser. No. 60/892,629, filed 2 Mar. 2007, which application is incorporated herein by reference.

FIELD OF THE INVENTION

The present invention is in the field of surgical apparatuses used in the treatment of diseases, wounds and other abnormal conditions of the bodies of humans and lower animal (Class 128). Specifically, the present invention relates to orthopedic instrumentation designed for particular use in a surgical procedure on bone structure to correct a deformity, fracture, unwanted or diseased condition Class 606/subclass 53). More specifically, the present invention relates to an osteotomy jig for use in bone reparation, to align a cutting means in a desired orientation for severing or partially severing a bone at a knee/knee joint so that a prosthetic member fitted thereto to effect the repair of the bone (subclasses 86-88).

BACKGROUND OF THE INVENTION

Total knee joint replacement surgery is now a common tool in the orthopedic surgeon's repertoire. However, there is a present controversy as to whether during a knee joint replacement surgery, the patella should be replaced as well. Some practitioners will replace the patella as well during the surgery if it is particularly worn. Other practitioners prefer to avoid replacing the patella at all costs. The controversy is difficult to resolve, because the patella replacement portion of a total knee replacement operation is the most poorly performed and understood aspect of the surgery. The standard full knee replacement surgery typically will balance the flexion gap and the extension gaps, but pay less attention to or overlook the patello-femoral gap.

The reason for this is at least in part because of the lack of appropriate alternative patellar jigs to guide the surgeon when replacing/resurfacing the patella. Typically, the patella is cut in isolation, i.e., separate and away from the femoral and tibial components of the replacement knee prosthesis. Because the patella is cut/resurfaced in isolation, it is difficult to easily assure the accuracy of the cutting/resurfacing of the patella to accommodate the flexion gap, the extension gap and the patello-femoral gap at the replacement knee joint.

It would be beneficial to the field to have an alternative patella jig that can not only be used in situ, but which also enables cutting of the patella with physical reference to the femoral prosthetic (or trial) component that it is to interface with. Additionally, it would be beneficial to have such alternative patella jig that can hold a range of patella sizes, without compromising accuracy of the physical interface alignment.

SUMMARY OF THE INVENTION

The present invention is a patellar fixing system for use, for example, in a total knee surgical procedure. The fixing system stabilizes a patella in situ in spatial/physical reference to the femoral prosthesis (or the femoral trial) to enable the appropriate cut to be made to the patella to assure the accuracy of the cutting/resurfacing of the patella to accommodate the patello-femoral gap at the replacement knee joint. The present system for resecting a patella in situ comprises a patella jig and a referencing component. The patella jig incorporates a patella clamp mechanism adapted to releaseably hold the patella. The femur referencing or engaging component provides a connection between the patella jig and an anchor point or landmark (i.e., a reference feature) on the femur. The connection to the anchor point or reference feature on the femur enables the patella jig to be oriented relative to the reference feature. Thus a patella held in the clamp mechanism can be fixed in an appropriate orientation relative to the femur during its resection. Cutting the patella while it is referenced to the patellar groove on the femur increases the accuracy of the resection relative to what otherwise may be accomplished.

The referencing feature on the femur can be accomplished in a number of manners. One is to install an artificial anchor point on the femur to serve as the reference feature via which the patella jig is connected to the femur. Another is to use the femoral prosthesis or trial which incorporate a feature that can be utilized as an anchor point. Additionally, a femur reference feature can be a natural surface feature of the femur itself, or can be a feature sculpted into the femur bone to serve this function.

DETAILED DESCRIPTION OF THE INVENTION

Referring now to the drawings, the details of preferred embodiments of the present invention are graphically and schematically illustrated. Like elements in the drawings are represented by like numbers, and any similar elements are represented by like numbers with a different lower case letter suffix.

Figure 1A:
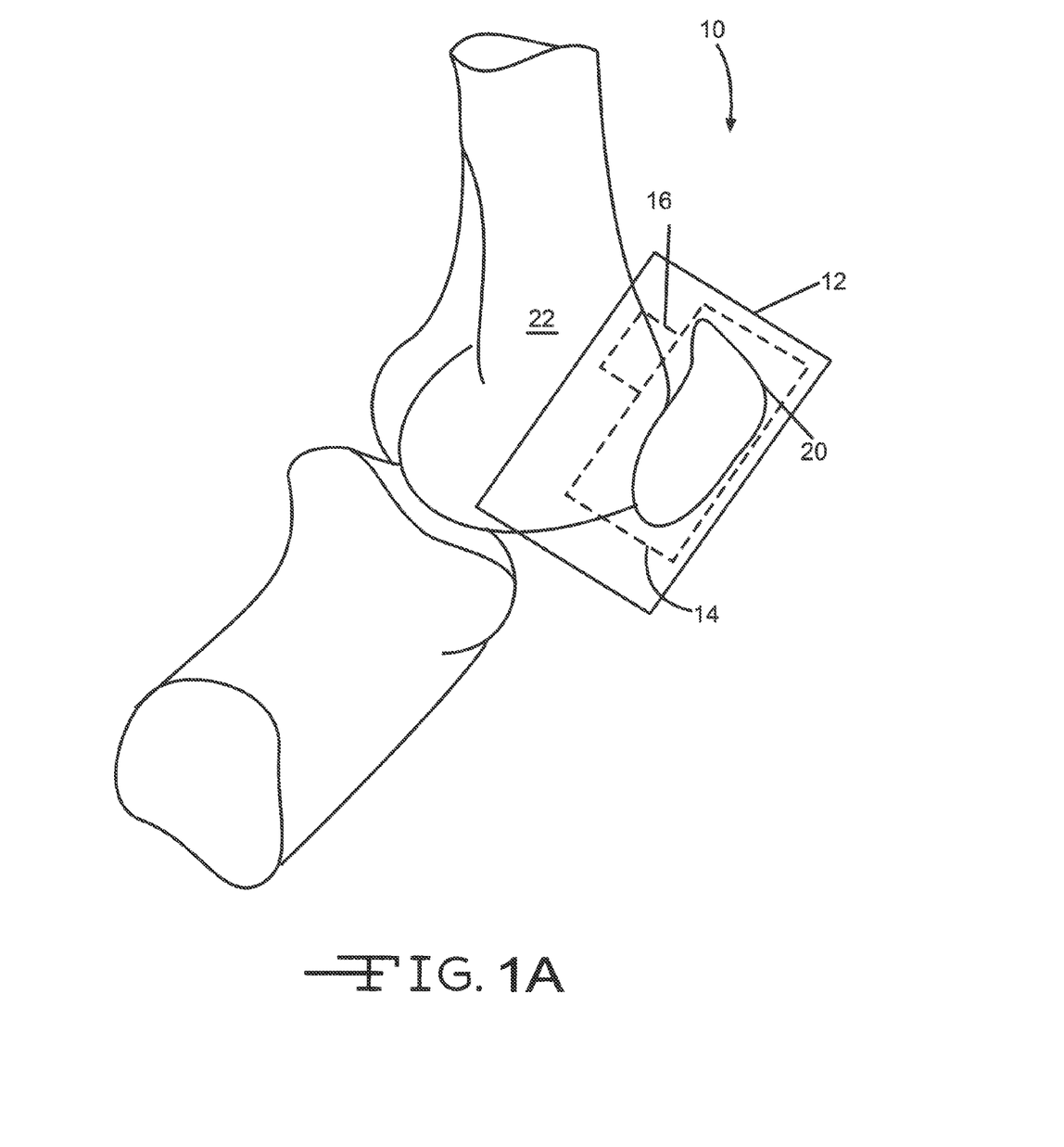
FIG. 1A is a schematic representation of the present patella fixing system showing the major components of the system in relationship to a patella and knee joint.

As exemplified in FIG. 1A, the present invention is an patellar fixing system 10 for use in situ in resecting a patella 20, in surgical procedures such as a knee joint replacement surgery. The system 10 includes a patella jig 12 comprised of a patella clamp mechanism 14 and a femur engaging component 16. The clamp mechanism 14 is adapted to releaseably grip and hold the patella 20 during its resection. Patella clamping mechanisms are known in the art. The femur engaging component 16 is adapted to interface with a femur reference feature 24a on a femur 22 and serves to connect the patella jig 14 to the reference feature 24a. This connection allows the clamping mechanism 14 of the patella jig 12 to be oriented relative to the surface of the femur 22, thus enabling a patella 20 gripped by the clamp mechanism 14 and disposed in the jig 12 in an appropriate aspect relative to the femur 22 for resection. Once the patella is set into the jig 12, it can be moved to a different position as necessary for resection without losing its aspect relative to the surface of the femur 22.

Figure 1B:
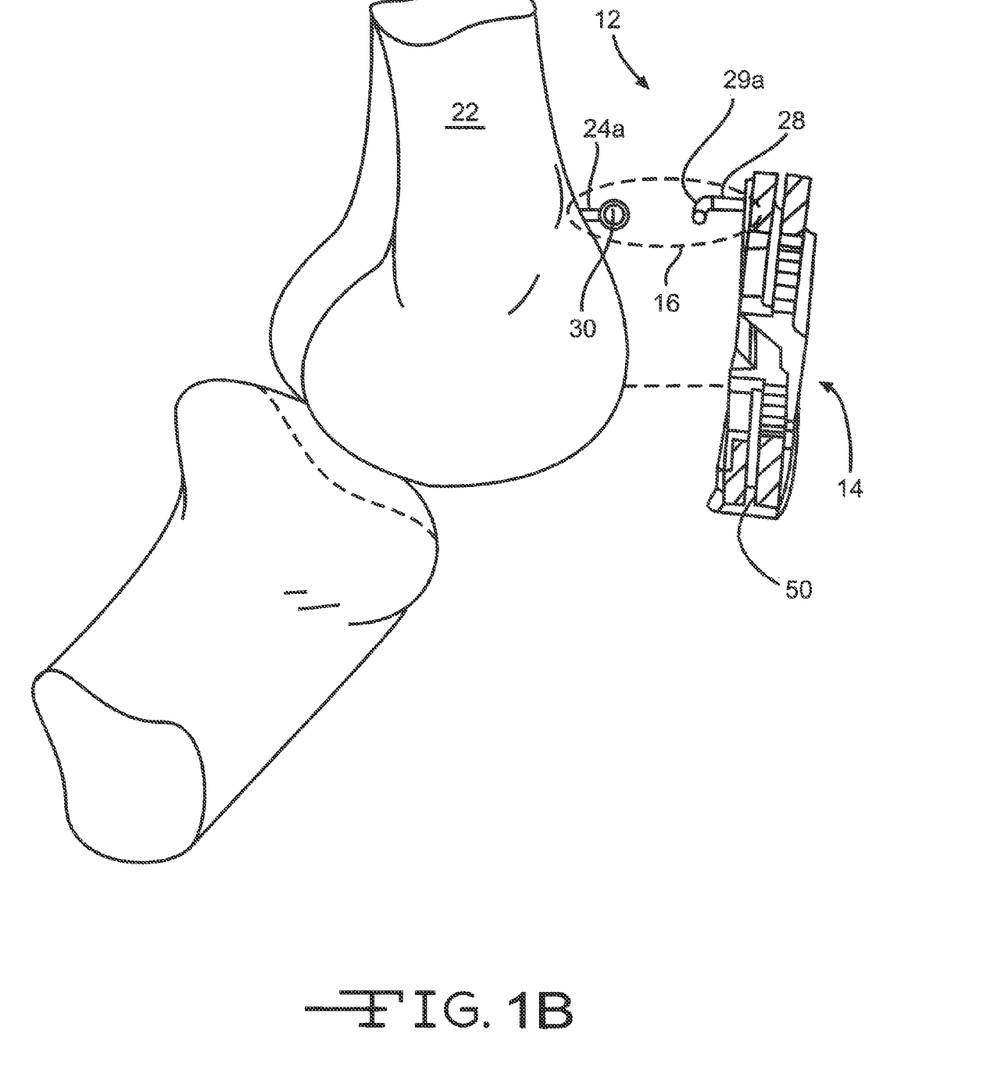
FIGS. 1B and 1C are perspective views of the knee joint bone showing alternative embodiments of femur features which can serve as a landmark/anchor point on the femur, relative to which orientation of the patella jig can be gauged.
Figure 1C:
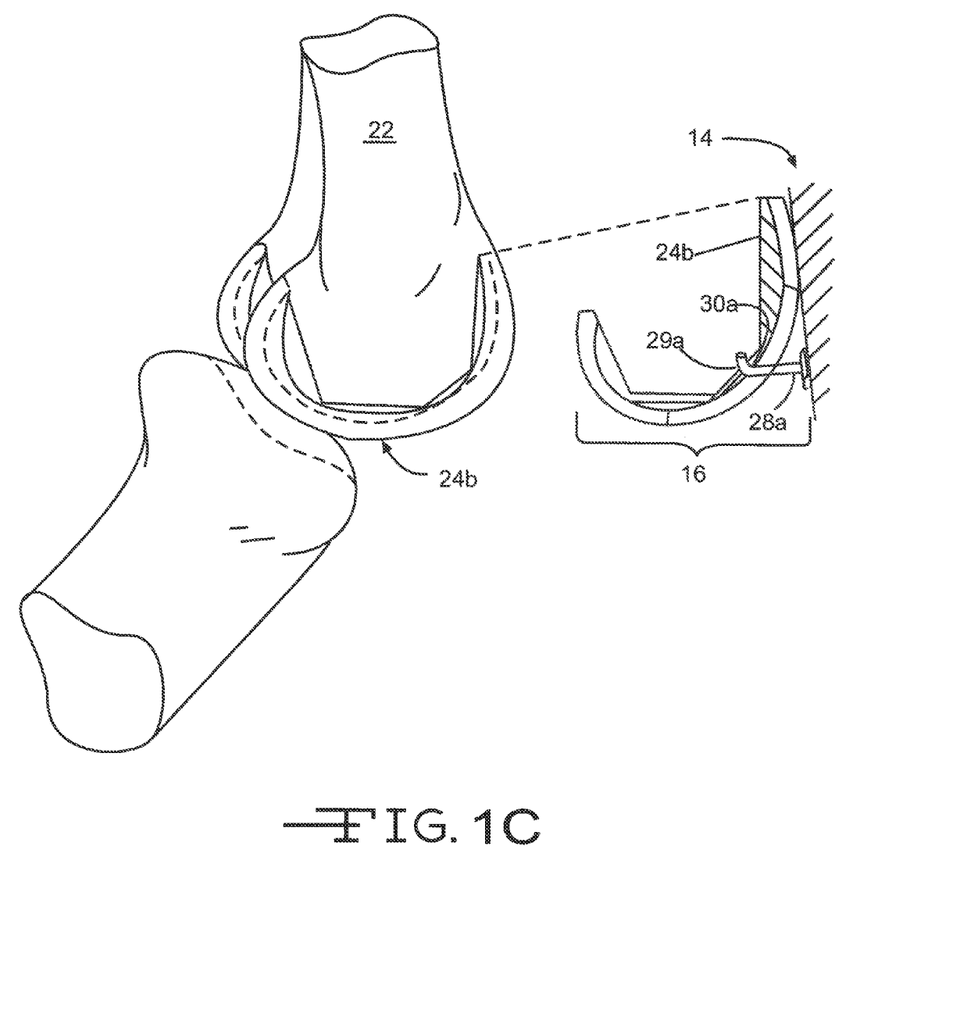

As exemplified in FIGS. 1B and 1C, the femur engaging component 16 is a mechanical linkage that comprises a jig link 28 fixed to the jig 12, and a femur reference fixture 24a that is installed on the femur 22. The jig link 28 releaseably connects the jig 12 to the femur reference fixture 24a installed on the femur 22, and enables the jig 12 to be disposed in an appropriate orientation relative to the femur 22. In FIG. 1B, the jig link 28 is a hook 28a and the femur reference fixture is a hook-eye fitting 24a that is fixed to the femur 22. The loop of the hook-eye fitting 24a is the linkage interface 30 of the jig link 28. The hook-eye fitting 24a fixed on the femur provides an anchor (or femur reference point) for the patella jig 12. The hook-eye of the reference fixture 24a is engageable by the link hook 28a to accomplish the purpose of the femur engaging component 16. In other words, the femur engaging mechanical linkage component 16 comprises a jig link 28 interfacing with a femur reference fixture 24a that provides an artificial physical reference point fixed on the femur 22.

Figure 2A:
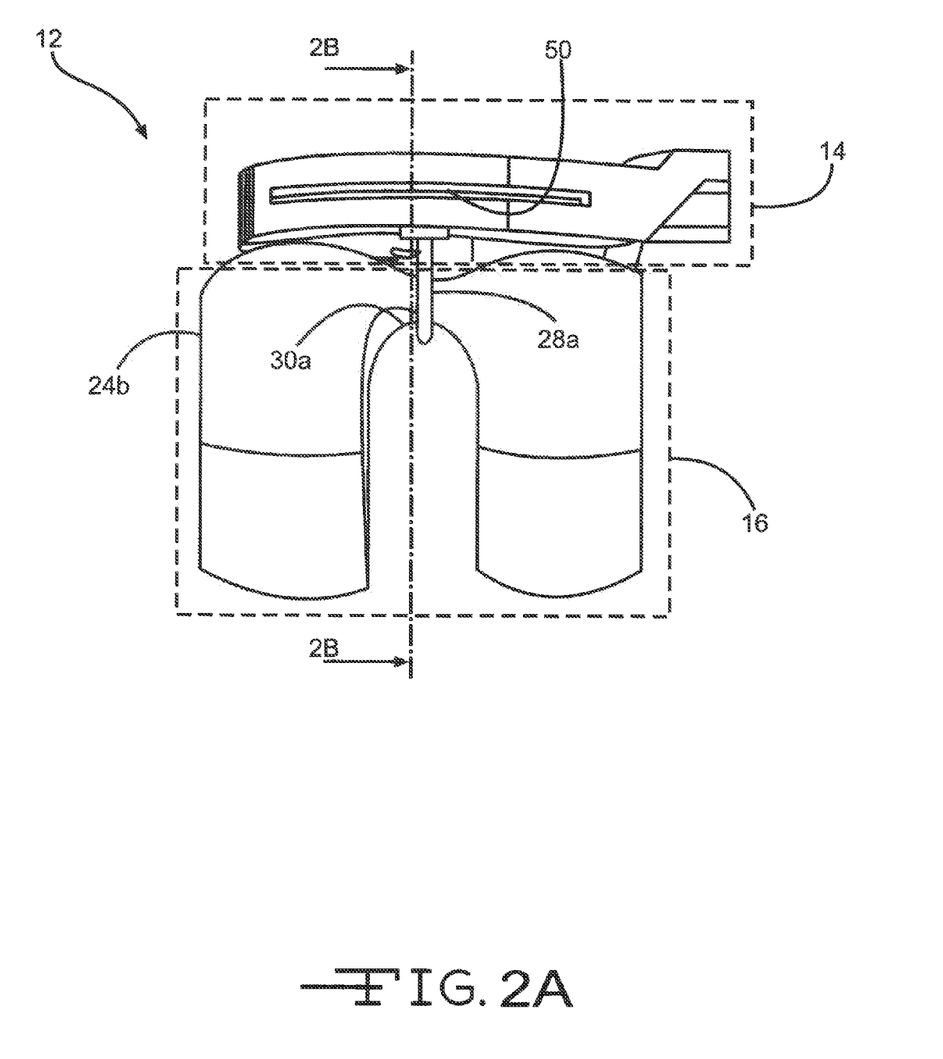
FIGS. 2A to 2C are schematic illustrations exemplifying an embodiment of the present patella jig, wherein the femur engaging component comprises a mechanical link to a prosthesis or trial.
Figure 2B:
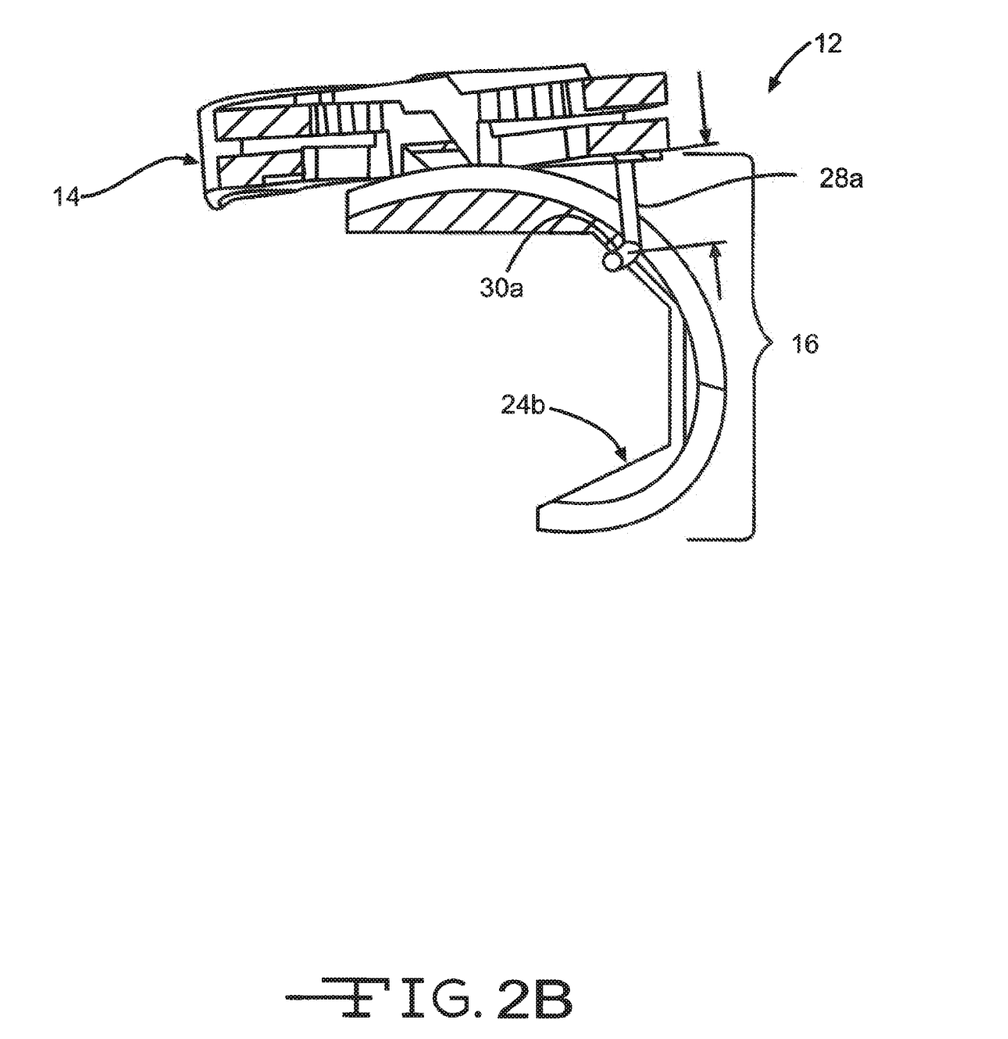
Figure 2C:
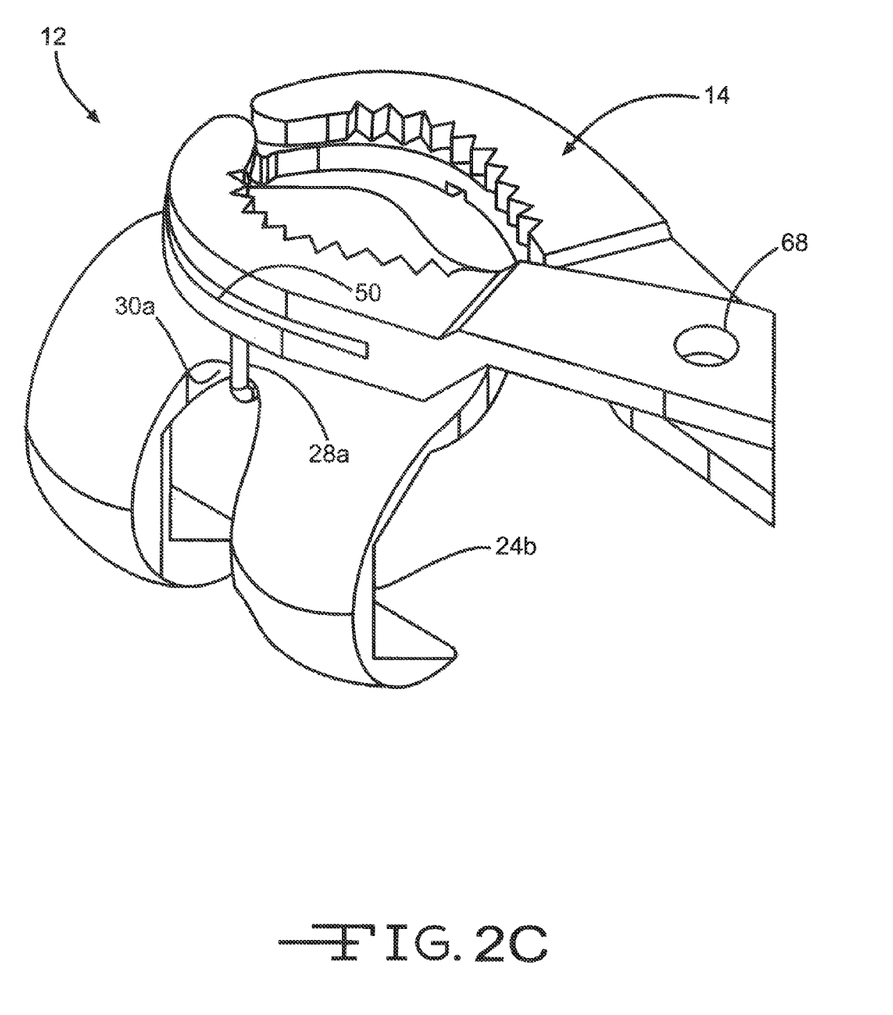
Figure 3A:
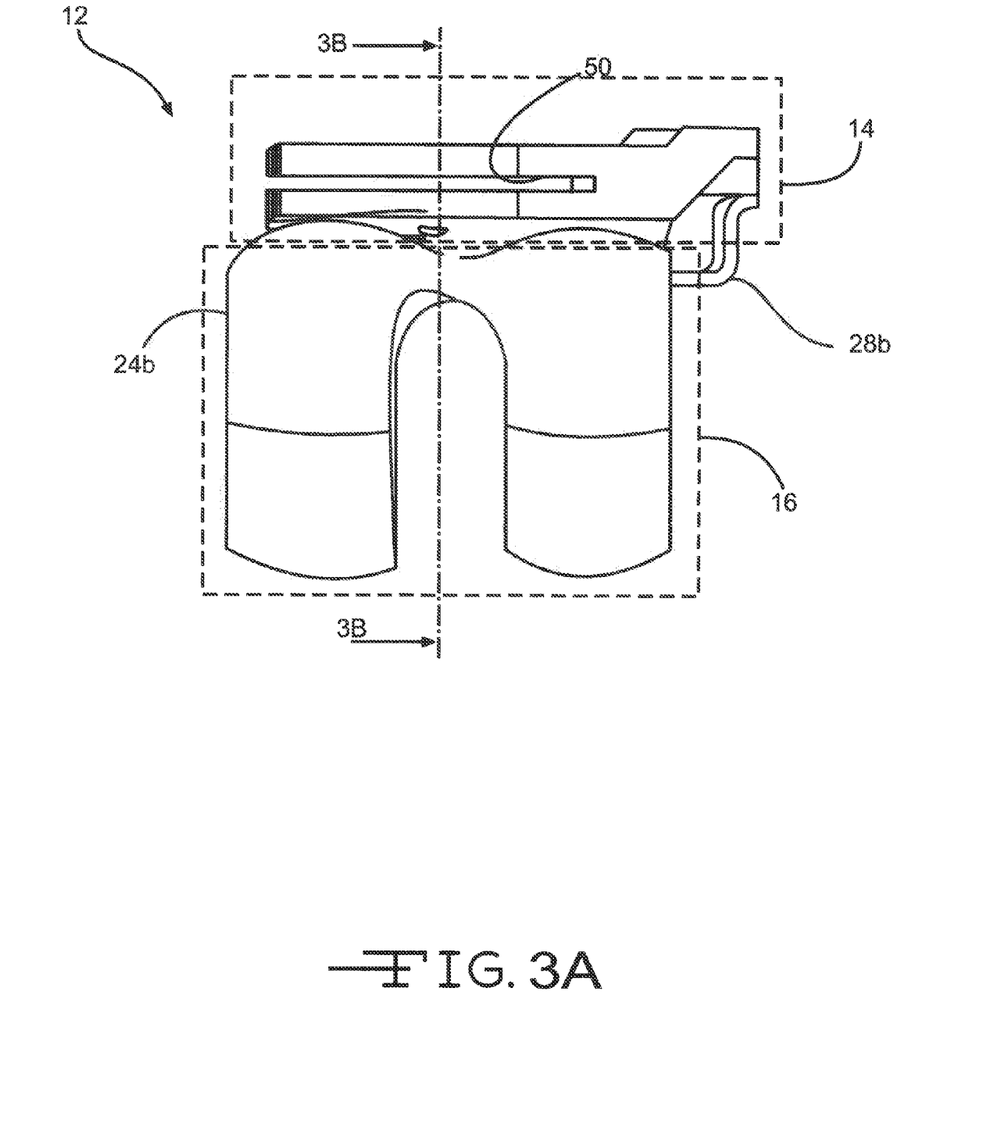
FIGS. 3A to 3E are schematic illustrations exemplifying an embodiment of the present patella jig, wherein the femur engaging component comprises an alternative mechanical link to a prosthesis or trial.
Figure 3B:
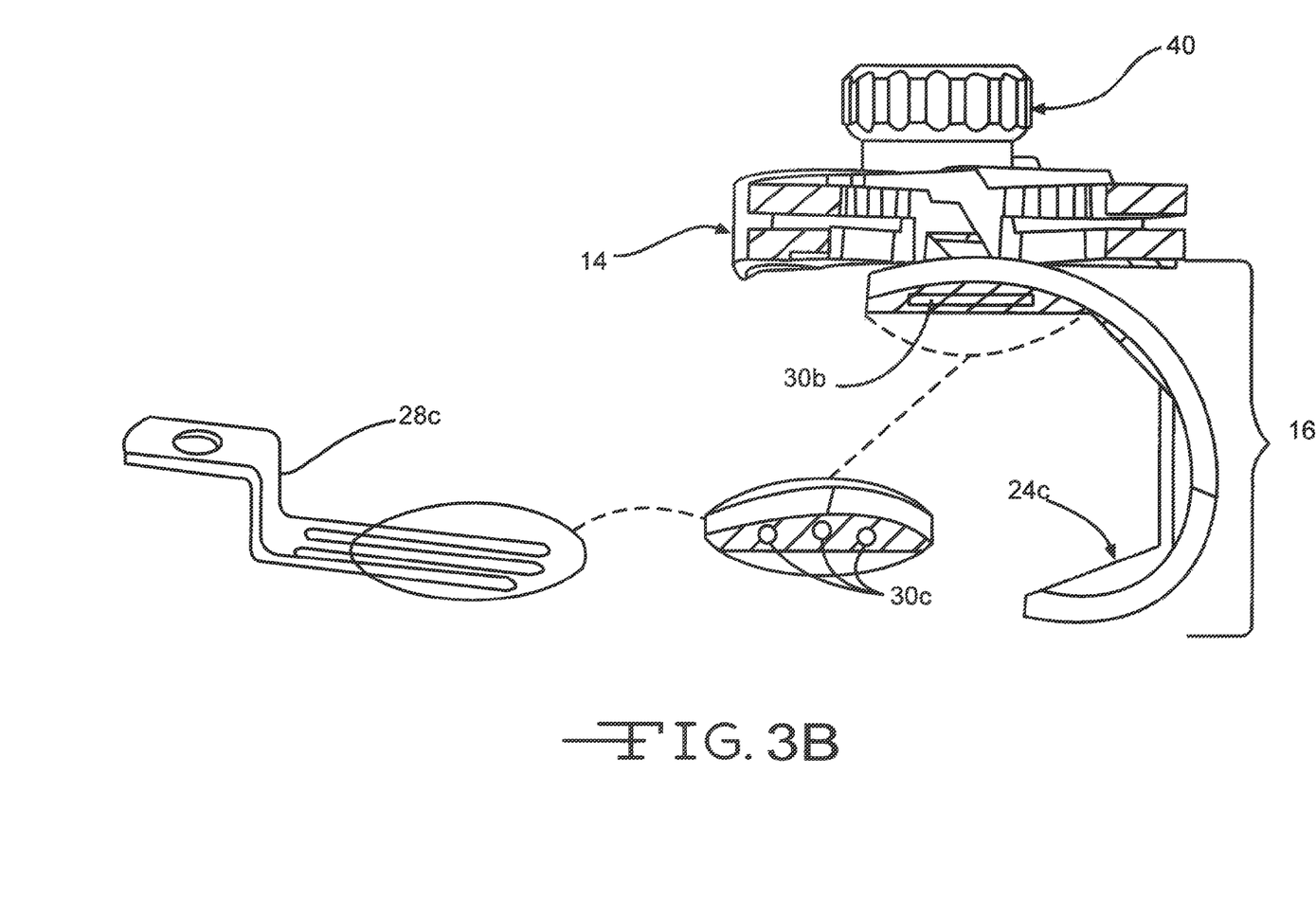
Figure 3C:
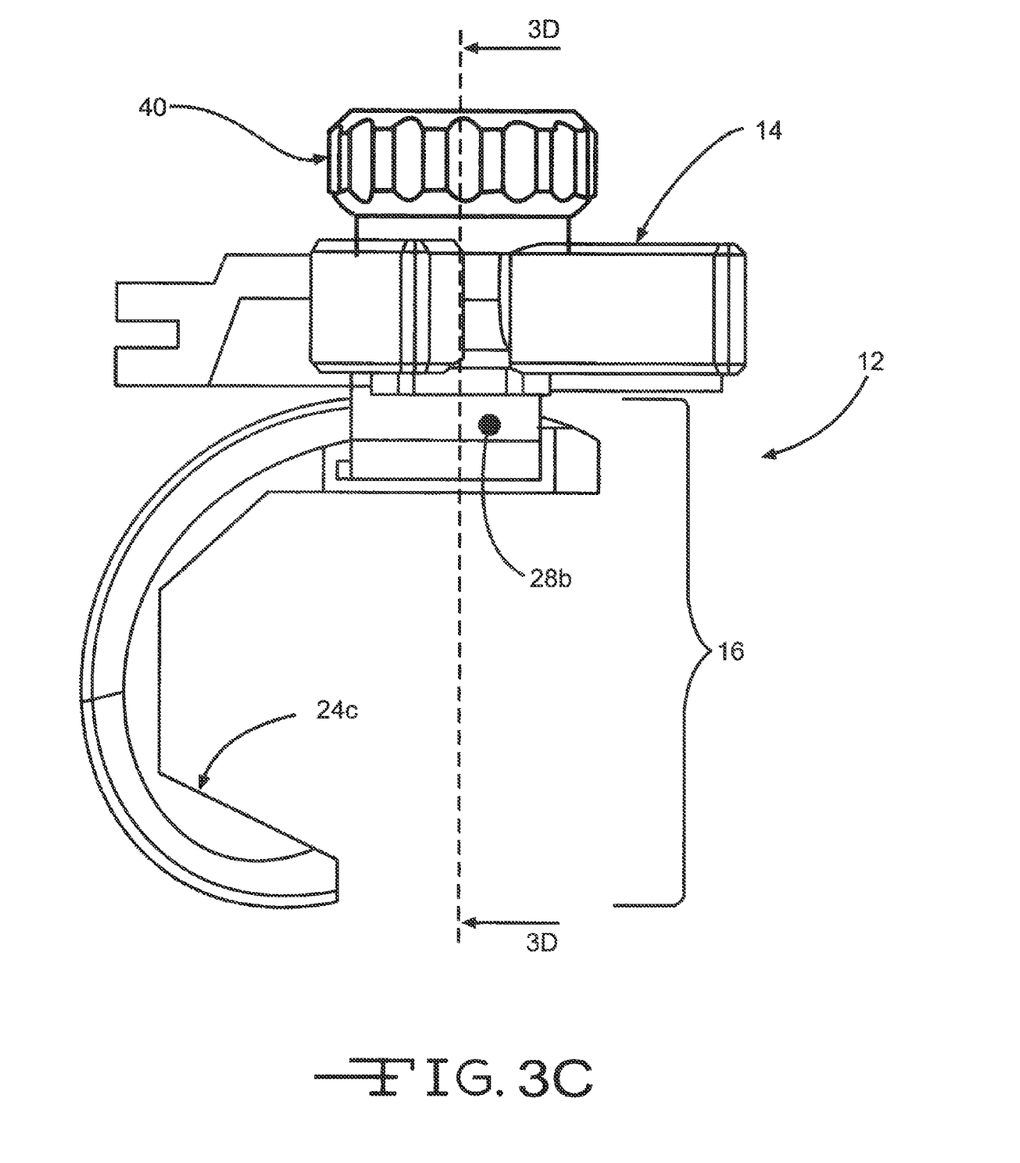
Figure 3D:
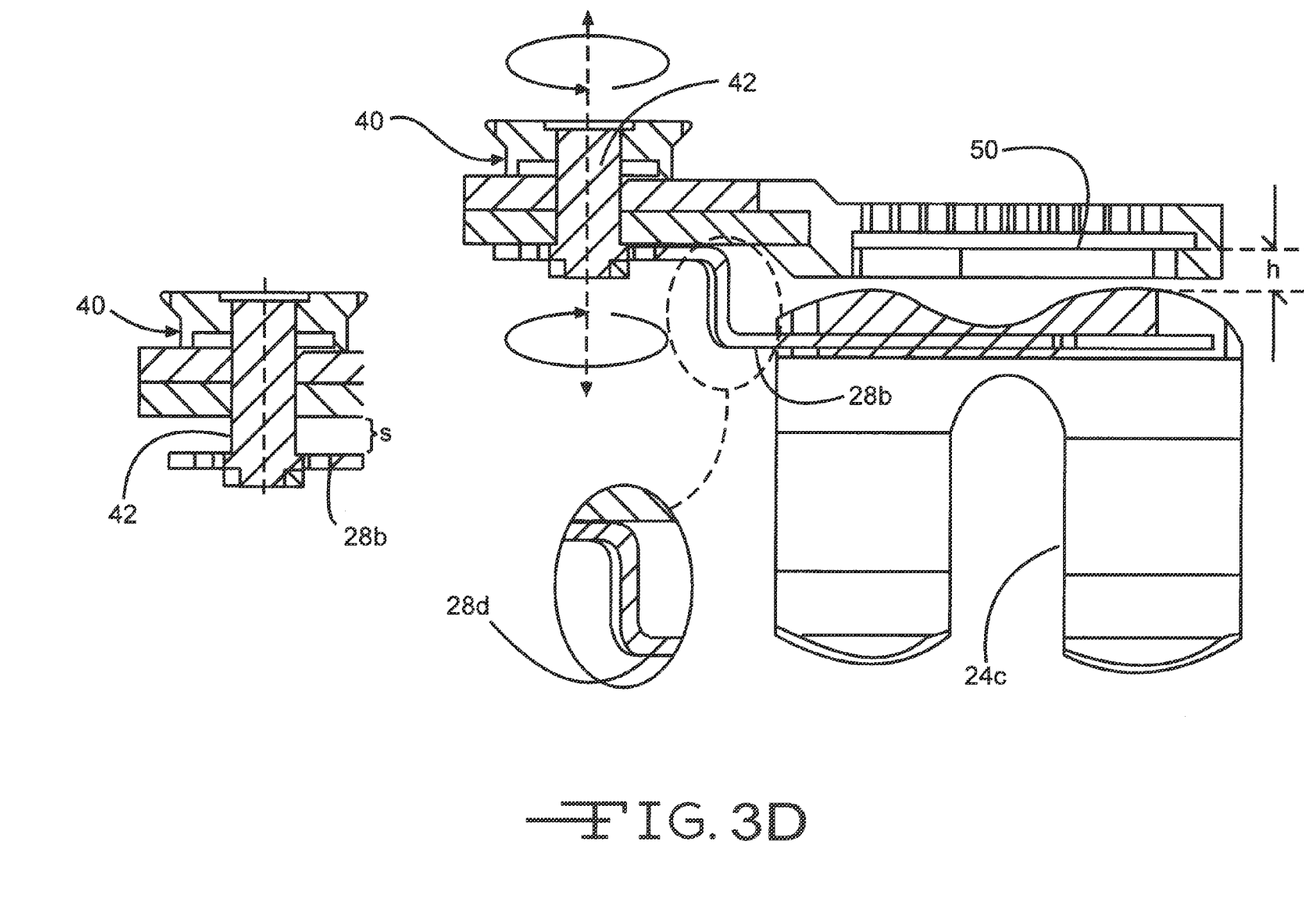
Figure 3E:
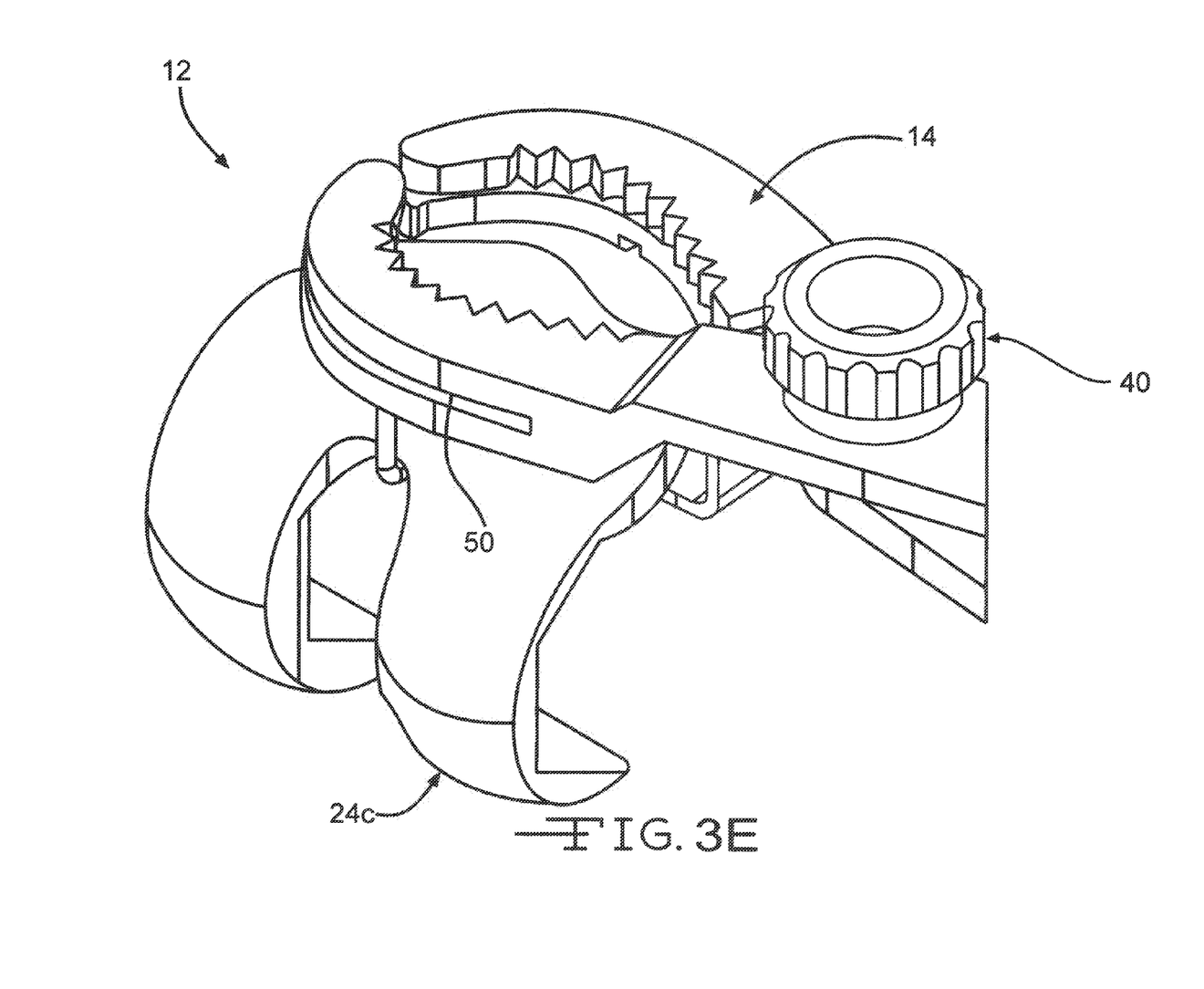
Figure 3F:
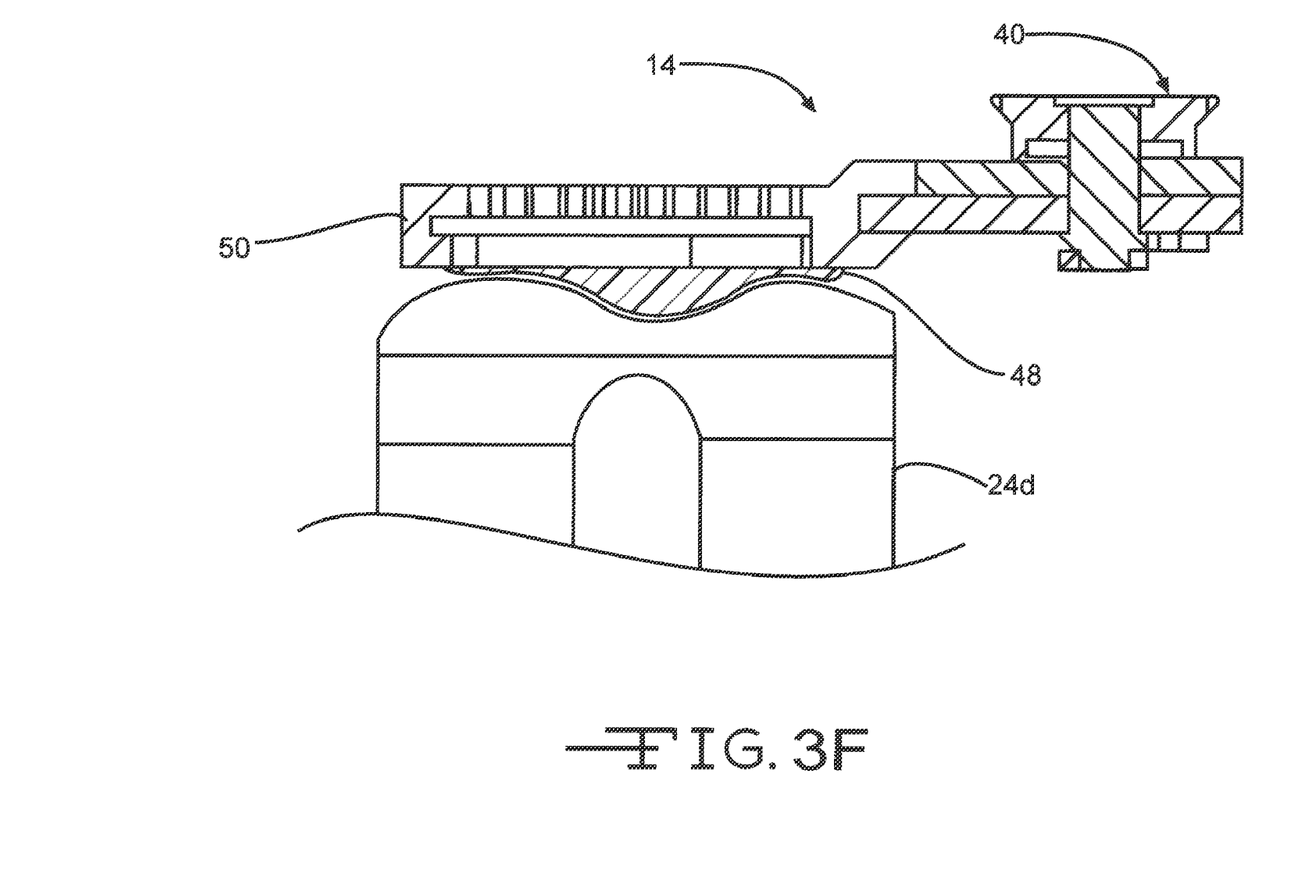
FIG. 3F is a schematic illustration exemplifying an embodiment of the present patella jig, wherein the femur engaging component comprises is not mechanically link to the prosthesis or trial, is connected via a complementary contoured interface pad.

FIG. 1C illustrates an example of a preferred artificial physical reference fixture, wherein the femur reference fixture installed on the femur 22 is a femoral prosthesis (or trial) device 24b. In this embodiment, the jig link 28 is a hook 28a, as in the embodiment of FIG. 1B. However, the femur reference fixture 24b is engageable by the link hook 28a at linkage interface 30b on the prosthesis device 24b to accomplish the purpose of the femur engaging component 16. See FIGS. 2A to 2C showing examples of the patella jig 12 of this embodiment.

FIGS. 3A to 3E illustrate examples of an alternative preferred embodiment. In this embodiment, the femur reference fixture installed on the femur 22 is also a femoral prosthesis (or trial) device 24b. However, the jig link 28 is a probe 28b configured as a flat blade, rather than as a hook 28a. Additionally, in this embodiment, the linkage interface 30b is integral to the prosthetic device 24c installed on the femur 22, and because of its configuration comprises a stabilized anchor point 30b. In this embodiment, the femur reference fixture 24c is preferably a trial device, rather than the finally installed prosthetic device, allowing the finally installed prosthesis to not have to incorporate the physical features of the linkage interface 30b. Additionally, the jig link probe 28b and its complementary linkage interface 30b can be configured other than as a blade. For example, the jig link probe 28c can be configured as a set of pins and the complementary linkage interface 30c configured as a set of pin bores 30c, as illustrated in the insets in FIG. 3B.

As can be seen in the figures, the clamp mechanism 14 of the patella resection jig 12 preferably includes a tool guide 50. The tool guide 50 may take various configurations selectable by the ordinary skilled artisan, but in the preferred embodiment exemplified, the tool guide is a miter slot through the jaws. The miter slot 50 is coplanar with and defines the resection plane of reversibly jig. The tool guide 50 is adapted to allow a cutting tool blade to pass through the jaws along the resection plane. The tool guide in the exemplified embodiment can be a closed miter slot 50 (see FIG. 2A) or can be an open miter slot 50a (see FIG. 3A).

Figure 4A:
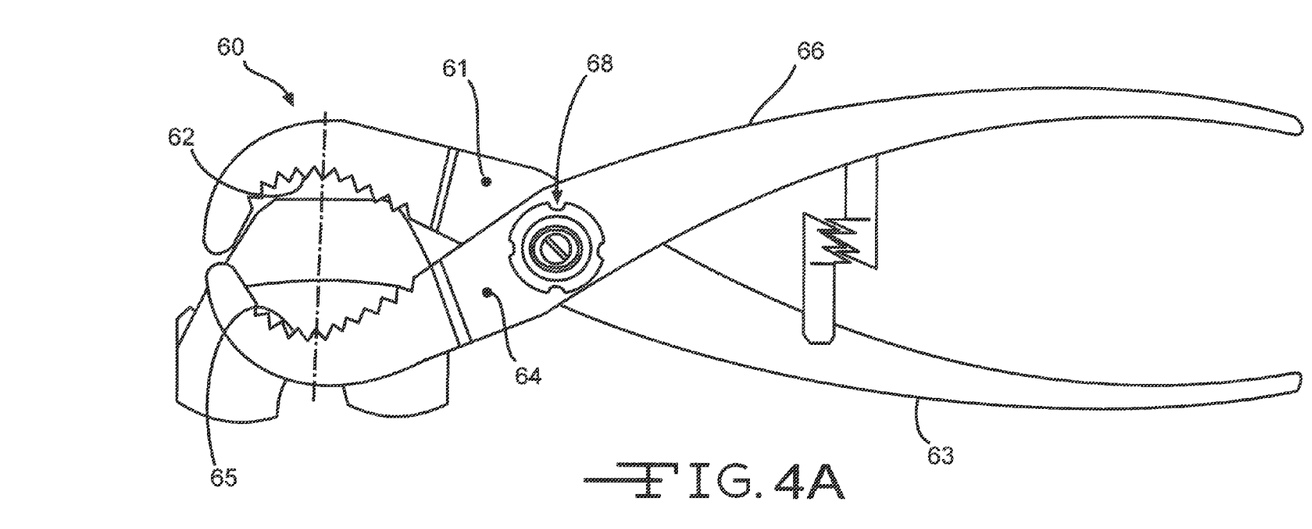
FIG. 4A is a schematic top plan view of the clamp mechanism of the patella jig configured as a pliers assembly.
Figure 4B:
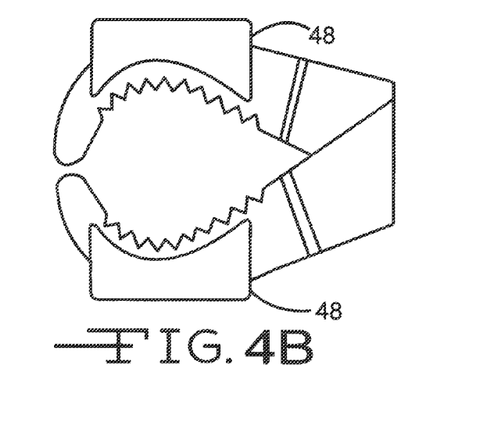
FIG. 4B is a schematic bottom plan view of the jaws of the clamp mechanism of FIG. 4A exemplifying an embodiment having complementary contoured interface pad for connecting the clamp mechanism to the prosthesis or trial.

In a preferred embodiment exemplifies by FIG. 4A, the patella clamp mechanism 14 comprises a hand-operated clamping pliers 60. The clamping pliers 60 have a first member 61 with a first jaw portion 62 and first handle portion 63, as well as a complementary second member 64 having an opposing second jaw portion 65 and a second handle portion 66. The first member and second member 61, 64 are reversibly joined at a pivot point 68 to form the clamping pliers 60. The jaws 62, 65 of the clamping pliers 60 are adapted to clamp onto the patella 20 at the periphery thereof. As exemplified in FIG. 4B, the jig link 28 projecting from bottom surface of the jaw of at least one member is a contoured pad 48. The contoured pad 48 is adapted to interface with the patellar surface of the femoral prosthesis device 24d when it is installed on the knee joint of the femoral bone 22.

Optionally, the patella resection jig 12 has a pivot assembly 40 for pivotably joining the first 61 and second 65 members together at the pivot point 68. In the embodiment illustrated (see FIGS. 3D and 3E), the pivot assembly 40 comprises a height adjustment mechanism 42 to adjust the spatial relationships of the jig link 28b of the femur engaging component 16 relative to the bottom surface of the jaws of the clamp mechanism 14. Additionally, the spatial relationship "s" of the jig link 28b relative to the bottom surface of the jaws can be adjusted by using a jig link 28d that has a different sized reach "r". See insert in FIG. 3D. It should be noted that the pivot assembly 40 is can be disassemble to allow separation of clamping mechanism 14 from the femur engaging component 16. That is in the same manner as it would be dissembled to change jig links. Disassembly in situ allows the surgeon to move the clamp mechanism 14 (with the patella 20 still clamped in it) away from the femur 22, and to flip/invert it as necessary in order to have good access and good visibility while performing the resection.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A patella clamp mechanism, comprising:
  a) a tool guide comprising opposed first and second jaws connected to each other at a proximal guide junction and being adapted to releaseably hold a patella, wherein the first and second jaws comprise aligned and opposed first and second miter slots; and
  b) a femur engaging component extending from an outer surface of the first jaw opposite the first miter slot, wherein the femur engaging component comprises a link portion extending along a longitudinal axis from a proximal link end secured to the outer surface of the first jaw opposite the first miter slot to a distal hook end with an imaginary extension of the link portion along the longitudinal axis extending through the first miter slot of the first jaw,
  c) wherein the distal hook end of the femur engaging component is detachably connectable to a reference feature on a femur to enable a patella to be held in the clamp mechanism at an appropriate orientation relative to the femur to enable resection of the patella along a resection plane defined by the first and second miter slots.

2. The patella clamp mechanism of claim 1 wherein the first and second miter slots are open at a distal end opposite the proximal guide junction.

3. The patella clamp mechanism of claim 1 comprising hand-operated clamping pliers having a first member with the first jaw and a first handle and a second member with the opposing second jaw and a second handle, the first member and the second member being joined to each other at a pivot point as the proximal guide junction to form the clamping pliers.

4. The patella clamp mechanism of claim 3, further comprising a pivot assembly for pivotably joining the first and second jaws together at the pivot point.

5. The patella clamp mechanism claim 4, wherein the pivot assembly is disassemblable to allow separation of the tool guide from the femur engaging component.

6. The patellar clamp mechanism of claim 1 wherein a contoured pad projects from the outer surface of the first jaw opposite the first miter slot.

7. A patellar fixing system for resecting a patella, the system including:
  a) a patella clamp mechanism, comprising:
    i) a tool guide comprising opposed first and second jaws connected to each other at a proximal guide junction and being adapted to releaseably hold a patella, wherein the first and second jaws comprise aligned and opposed first and second miter slots; and
    ii) a femur engaging component extending from an outer surface of the first jaw opposite the first miter slot, wherein the femur engaging component comprises a link portion extending along a longitudinal axis from a proximal link end secured to the outer surface of the first jaw opposite the first miter slot to a distal hook end with an imaginary extension of the link portion along the longitudinal axis extending through the first miter slot of the first jaw;
  b) a femoral prosthesis device installable on a femur, the prosthesis device having an integral femur reference feature which is adapted to interface with the femur engaging component; and
  c) wherein the patella clamp mechanism may be oriented via the femur engaging component relative to the femur reference feature to dispose a patella in the tool guide in an appropriate orientation relative to the femur for resecting the patella along a resection plane defined by the first and second miter slots.

8. A femoral prosthesis device comprising a femur reference feature adapted to be detachably connectable to a patella clamp mechanism according to claim 1 when the femoral prosthesis device is installed on a femoral bone.

9. The patella clamp mechanism of claim 1 wherein the first and second miter slots are closed at a distal end opposite the proximal guide junction.

10. The patella clamp mechanism of claim 4 wherein the pivot assembly comprises a height adjustment mechanism to adjust a spatial relationship of the femur engaging component with respect to the tool guide.

11. A patella clamp mechanism, comprising:
  a) a tool guide comprising opposed first and second jaws connected to each other at a proximal guide junction and being adapted to releaseably hold a patella, wherein the first and second jaws comprise aligned and opposed first and second miter slots; and
  b) a femur engaging component extending from an outer surface of the first jaw opposite the first miter slot, wherein the femur engaging component comprises a link portion extending along a longitudinal axis from a proximal link end secured to the outer surface of the first jaw opposite the first miter slot to a distal blade with an imaginary extension of the link portion along the longitudinal axis extending through the first miter slot of the first jaw,
  c) wherein the distal blade of the link portion of the femur engaging component is detachably connectable to a reference feature on a femur to enable a patella to be held in the tool guide at an appropriate orientation relative to the femur to enable resection of the patella along a resection plane defined by the first and second miter slots.

12. The patella clamp mechanism of claim 11 wherein the distal blade of the femur engaging component comprises a set of pins defined by the first and second miter slots.

13. The patella clamp mechanism of claim 11 wherein the first and second miter slots are open at a distal end opposite the proximal guide junction.

14. The patella clamp mechanism of claim 11 wherein the first and second miter slots are closed at a distal end opposite the proximal guide junction.

15. The patella clamp mechanism of claim 11 comprising hand-operated clamping pliers having a first member with the first jaw and a first handle and a second member with the opposing second jaw and a second handle, the first member and the second member being joined to each other at a pivot point as the proximal guide junction to form the clamping pliers.

16. The patella clamp mechanism of claim 15 further comprising a pivot assembly for pivotably joining the first and second jaws together at the pivot point.

17. The patella clamp mechanism of claim 16 wherein the pivot assembly is disassemblable to allow separation of the tool guide from the femur engaging component.

18. The patella clamp mechanism of claim 16 wherein the pivot assembly comprises a height adjustment mechanism to adjust a spatial relationship of the femur engaging component with respect to the tool guide.

19. The patellar clamp mechanism of claim 11 wherein a contoured pad projects from the outer surface of the first jaw opposite the first miter slot.

* * * * *